United States Patent [19]

Cassidy et al.

[11] 4,341,708
[45] Jul. 27, 1982

[54] PROSTACYCLIN AZA ANALOGUE INTERMEDIATES

[75] Inventors: Frederick Cassidy, Harlow; Keith H. Baggaley, Redhill; Arthur W. R. Tyrrell, Reigate, all of England

[73] Assignee: Beecham Group Limited, England

[21] Appl. No.: 230,539

[22] Filed: Feb. 2, 1981

Related U.S. Application Data

[62] Division of Ser. No. 82,713, Oct. 9, 1979, Pat. No. 4,262,008.

[30] Foreign Application Priority Data

Oct. 14, 1978 [GB] United Kingdom .............. 40597/78

[51] Int. Cl.$^3$ .......................................... C07D 491/048
[52] U.S. Cl. ........................ 260/326.29; 260/326.45; 260/326.46; 260/326.5 B; 424/274; 560/170
[58] Field of Search .................................... 260/326.29

[56] References Cited

U.S. PATENT DOCUMENTS 4,262,008 4/1981 Cassidy et al. ..................... 424/274

FOREIGN PATENT DOCUMENTS 2720999 10/1977 Fed. Rep. of Germany .

Primary Examiner—Mary C. Lee
Attorney, Agent, or Firm—Jacobs & Jacobs

[57] ABSTRACT

An intermediate compound which is a perhydrofuro [3,2-b] pyrrole of the formula:

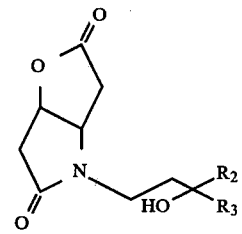

wherein:
$R_2$ is hydrogen or $C_{1-4}$ alkyl; and
$R_3$ is $C_{4-9}$ alkyl, $C_{5-7}$ cycloalkyl or $C_{5-7}$ cycloalkyl $C_{1-6}$ alkyl;

for use in the synthesis of prostacyclin aza analogues having anti-thrombotic activity.

1 Claim, No Drawings

1 …

PROSTACYCLIN AZA ANALOGUE INTERMEDIATES

CROSS-REFERENCE

This is a division of Ser. No. 082,713 filed Oct. 9, 1979.

This invention relates to novel compounds having useful pharmacological activity, to pharmaceutical compositions containing these compounds, and to processes for their preparation.

Belgian Pat. No. 854463 describes compounds of formula (A):

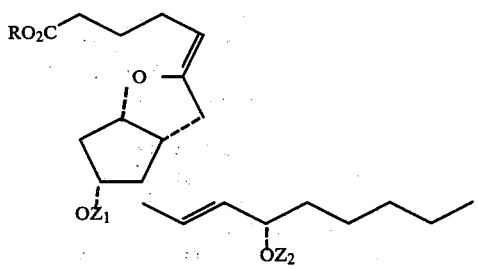

(A)

wherein R is hydrogen or a cation such as sodium and $Z_1$ and $Z_2$ are hydrogen or a blocking radical such as acyl or trialkylsilyl. It is stated in this Patent that prostacyclin (the compound of formula (A) wherein R, $Z_1$ and $Z_2$ are all hydrogen) has strong antiaggregation effect on blood platelets and may be used in the prophylaxis and treatment of thromboses, and also has other activities.

We have now discovered a class of compounds which are structurally distinct from those compounds described in Belgian Pat. No. 854463 and which have a useful antiaggregation effect on blood platelets and bronchodilator activity.

Accordingly the present invention provides a compound of formula (I):

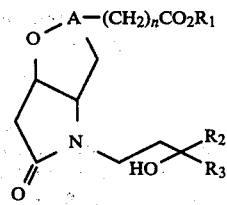

(I)

wherein:

A is >CH— and n is 1 to 6; or
A is >C=CH— and n is 0 to 5; or
A is >CH— CH=CH— and n is 0 to 4; and
$R_1$ is hydrogen or $C_{1-6}$ alkyl;
$R_2$ is hydrogen or $C_{1-4}$ alkyl; and
$R_3$ is $C_{4-9}$ alkyl, $C_{5-7}$ cycloalkyl or $C_{5-7}$ cycloalkyl-$C_{1-6}$ alkyl; and salts thereof.

When A is >CH and n is 1 to 6, suitably n is 3 to 6, for example 4 or 6, preferably 4.

When A is >C=CH— and n is 0 to 5, suitably n is 2 to 5, for example 3 or 5, preferably 3.

When A is >CH—CH=CH— and n is 0 to 4, suitably n is 1 to 4, for example 2 or 4, preferably 2.

It is believed that preferred groups A-$(CH_2)_n$-include >CH—$(CH_2)_{n'}$— wherein n' is 3 to 6, preferably 4.

Suitable examples of $R_1$ include hydrogen and $C_{1-4}$ alkyl, such as methyl, ethyl, n and iso-propyl and n-butyl. More suitably $R_1$ is hydrogen, methyl or ethyl.

$R_2$ may suitably be hydrogen, methyl or ethyl. Preferred $R_2$ groups include methyl.

Suitable groups $R_3$ when $R_3$ is $C_{4-9}$ alkyl include straight chain alkyl groups, such as n-butyl, n-pentyl, n-hexyl and n-heptyl, or alkyl groups branched by one or two methyl groups (at the same or different carbon atoms). Thus for example, $R_3$ may be a group $CH_2R_4$, $CH(CH_3)R_4$ or $C(CH_3)_2R_4$, wherein $R_4$ is a straight chain alkyl group such that the carbon content of the resultant group $R_3$ is 4 to 9.

In general preferred groups $R_3$ when $R_3$ is an alkyl group include straight chain pentyl, hexyl and heptyl groups. Of these straight chain hexyl is often the most useful. Other preferred groups $R_3$ include groups $CH(CH_3)R_4$ and $C(CH_3)_2R_4$ wherein $R_4$ is straight chain butyl, pentyl and hexyl.

When $R_3$ is or contains a $C_{5-7}$ cycloalkyl moiety, the moiety may suitably be a cyclohexyl moiety. Examples of suitable $C_{1-6}$ alkyl moieties when $R_3$ is a $C_{5-7}$ cycloalkyl-$C_{1-6}$ alkyl group include methyl, ethyl, propyl, butyl and amyl.

The compounds of formula (I) may form conventional salts of their carboxyl functions. Such salts include those with alkali and alkaline earth metals, suitably sodium and potassium, and ammonium and substituted ammonium satls.

From the aforesaid it can be seen that a preferred sub-group of compounds within formula (I) is of formula (II):

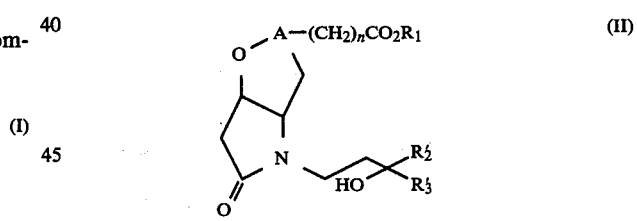

(II)

wherein:

A, n and $R_1$ are as defined for formula (I);
$R_2'$ is hydrogen, methyl or ethyl; and
$R_3'$ is $C_{4-9}$ alkyl; and salts thereof In formula (II) suitable and preferred examples of A and n are as described in relation to formula (I). Most preferred examples of A and n include those such that A—$(CH_2)_n$— is a group >CH—$(CH_2)_{n'}$— wherein n' is 3 to 6, for example 4 or 6, preferably 4.

Suitable and preferred groups $R_1$ are as described hereinbefore in regard to formula (I).

Preferably $R_2'$ is methyl.

Suitable and preferred groups $R_3'$ include those groups hereinbefore described for $R_3$ when $R_3$ is $C_{4-9}$ alkyl.

Within formula (II), a particularly useful group of compounds is of formula (III):

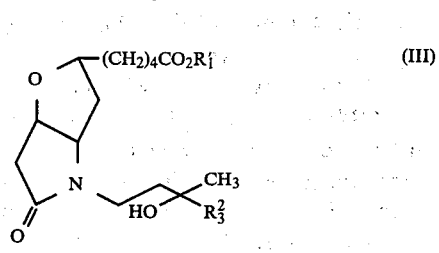

wherein:

$R_1'$ is hydrogen or $C_{1-4}$ alkyl; and $R_3^2$ is a straight chain $C_{5-7}$ alkyl group; and salts thereof.

Suitably in formula (III) $R_1$ is hydrogen, methyl or ethyl.

Also, suitably in formula (III) $R_3^2$ is n-hexyl.

Within the compounds of formula (I) there is a sub-group of formula (IV):

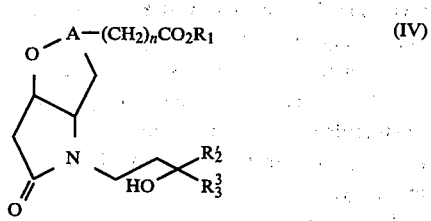

wherein:

A, n, $R_1$ and $R_2^1$ are as defined in formula (II); and $R_3^3$ is a group of formula (V):

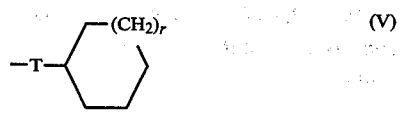

wherein:

T is a bond or a $C_{1-6}$ alkylene group and r is 0, 1 or 2.

In formula (IV) suitable and preferred examples of A, n, $R_1$ and $R_2^1$ are as described in relation to formula (II).

In formula (V) r is preferably 1.

In formula (V) T is suitably a bond, methylene or ethylene; preferably a bond.

The invention also provides a process for the preparation of the compounds of the formula (I), which process comprises (i) demercuration, (ii) dehydrohalogenation or (iii) oxidation of a compound of formula (VI):

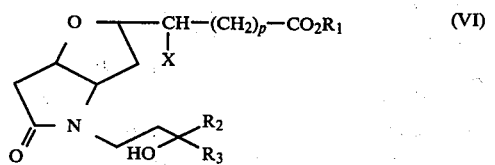

wherein $R_1$, $R_2$ and $R_3$ are as defined in formula (I), p is 0 to 5 and X is (i) a mercuri salt, (ii) halo or (iii) phenyl selenyl respectively.

The demercuration of a compound of formula (VI) wherein X is a mercuri salt yields a compound of formula (I) wherein A is $>CH-$ and n is 1 to 6. This reaction may suitably be carried out with a agent such as sodium borohydride. Suitable mercuri salt X include trifluoracetate.

The dehydrohalogenation of a compound of formula (VI) wherein X is halo yields a compound of formula (I) wherein A is $>C=CH-$ and n is 0 to 5. This reaction may suitably be carried out by reaction with a base such as potassium t-butoxide, or other alkali metal alkoxide, 1,5-diazabicyclo [4.3.0]-non-5-ene or 1,5-diazabicyclo [5.4.0] undec-5-ene.

The oxidation of a compound of formula (VI) wherein X is phenyl selenyl yields a compound of formula (I) wherein A is $>CH-CH=CH-$ and n is 0 to 4. This reaction may suitably be carried out with an oxidising agent such as hydrogen peroxide.

After the cyclisation reaction $R_1$ may be varied as desired. For example an $R_1$ ester group may be de-esterified in conventional manner to give the corresponding acid. Also compounds of formula (I) wherein $R_1$ is hydrogen may be converted to salts in the usual manner.

The preparation of the intermediates of formula (VI), which compounds are novel and as useful intermediates form an important aspect of this invention, depends on the nature of the X substitutent.

When X is a mercuri salt, the corresponding compound of the formula (VI) may be prepared by reacting a compound of formula (VII):

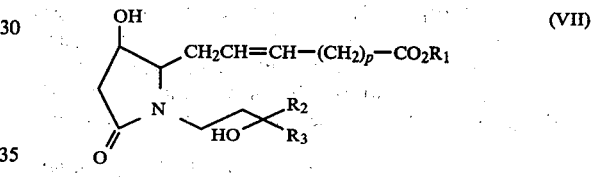

wherein the variables are as defined in formula (I), and p is 0 to 5, with a mercuri (II) salt, such as mercuric trifluoroacetate.

When X is halo, the compound of formula (VI) may be prepared by reaction of a compound of formula (VII) with a halogenating agent such as N-bromosuccinimide or iodine or like source of positive halogen.

When X is phenyl selenyl, the compound of formula (VI) may be prepared by reaction of a compound of formula (VII) with a phenyl selenyl halide such as the bromide.

Reactions of the general nature described above may be carried as described in the literature, for example E. J. Corey et al, J. Am. Chem. Soc., 1977, 99, 2006.

Intermediate compounds of the formula (VII) may be prepared by reduction of the corresponding compound of formula (VIII):

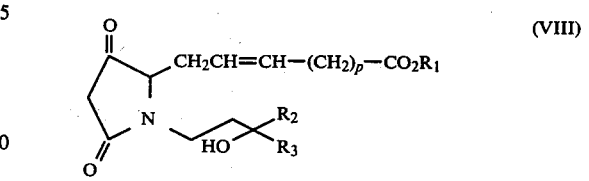

This reaction may suitably be carried out with sodium borohydride or lithium perhydro-9b-boro-phenalylhydride under conventional conditions.

Compounds of the formula (VIII) may be prepared by decarboxylation of the corresponding compound of formula (IX):

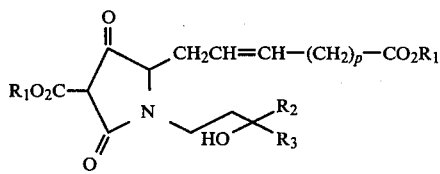
(IX)

in the general manner described in U.K. Pat. No. 1,524,818.

Compounds of the formula (IX) may be prepared by cyclisation of a compound of formula (X):

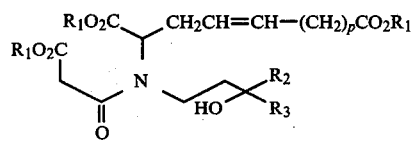
(X)

in the general manner described in U.K. Pat. No. 1,524,818.

Compounds of the formula (X) may be prepared by acylation of the corresponding compound of formula (XI):

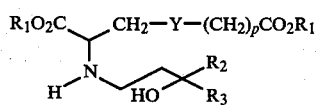
(XI)

wherein Y is —CH=CH— or —C≡C—, in the general manner described in U.K. Patent No. 1,524,818, followed by reduction of the Y group to —CH=CH— if necessary.

Compounds of the formula (XI), and their preparation, are fully described in the published literature, such as U.K. Pat. No. 1,524,818 and West German Offenlegungsschrift No. 2,724,948. Thus the desired compound of the formula (XI) may be prepared by any process described in these publications, or by a process analogous thereto.

In an alternative synthetic procedure, the intermediates of formula (VII) as hereinbefore defined may be prepared by a Wittig reaction on a compound of formula (XII):

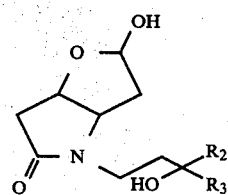
(XII)

Suitably this reaction is carried out using a substituted phosphonium halide such as triphenyl (4-carboxybutyl)-phosphonium bromide, in the presence of a strong base such as sodium hydride in dimethyl sulphoxide.

The compounds of formula (XII) may themselves be prepared from compounds of formula (XIII):

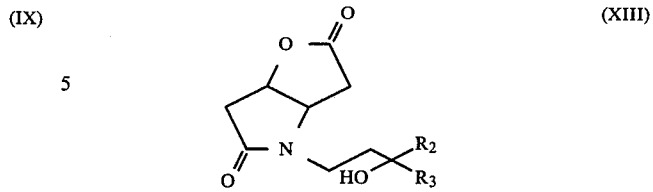
(XIII)

by reduction. This reduction can be carried out with di-isobutylaluminium hydride in a suitable solvent such as hexane or toluene, or, more suitably, with lithium tri-tert-butoxyaluminohydride in a solvent such as tetrahydrofuran.

It is believed that compounds of the formula (XII) and (XIII) are novel compounds, and as useful intermediates form an important aspect of this invention.

The compounds of formula (XIII) may be prepared from compounds of the formula (XIV):

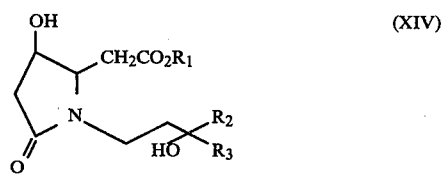
(XIV)

by a cyclisation reaction carried out under dehydrating conditions, for example heating in benzene or toluene in the presence of a catalyst such as toluene-p-sulphonic acid.

Compounds of formula (XIV) may be prepared in an analogous manner to the synthetic procedure described hereinbefore for compounds of formula (VII), and need not be isolated prior to conversion to the corresponding compound of the formula (XIII).

In yet another variation, the afore defined intermediate compounds of formula (XII) may be prepared by reaction of a compound of formula (XV):

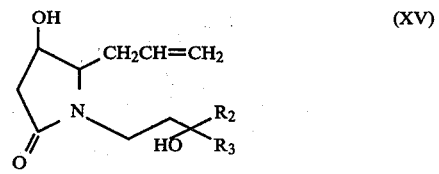
(XV)

to cleave the double bond.

This reaction is suitably carried out under mild oxidation, for example by ozonolysis or by reaction with sodium periodate in the presence of osmium tetroxide, and proceeds by giving an aldehyde of formula (XII)[1]:

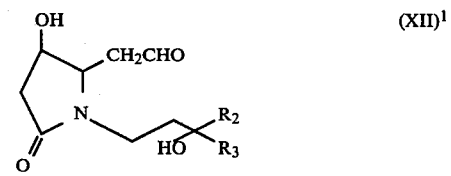
(XII)[1]

which exists as the desired cyclic lactol of formula (XII)

The compounds of formula (XV) may themselves in turn be prepared by reduction of the corresponding compound of formula (XVI):

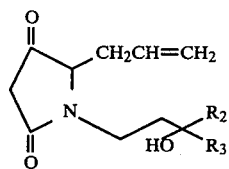

with a suitable reagent such as a sodium borohydride.

Of course the compounds of the formula (XVI) may be prepared in analogous manner to the preparation of the compounds of the formula (VIII), as hereinbefore described.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The compounds of the formula (I) have useful pharmacological activity.

For example the compounds of the formula (I) have platelet aggregation inhibition activity, and therefore may be used for the treatment and prophylaxis of venous throbosis and also for preventing platelet aggregation in ex vivo blood supplies. It is envisaged that this anti-platelet aggregation activity of the compounds will be their activity of prime importance.

The compounds of the formula (I) also have bronchodilation activity, and thus may be used as bronchodilators in the treatment and prophylaxis of diseases related to bronchoconstriction such as bronchial asthma.

In use, the compounds of the formula (I) will be formulated as pharmaceutical compositions.

Thus the invention also provides a pharmaceutical composition comprising a compound of the formula (I) and a pharmaceutically acceptable carrier.

Clearly the formulation of the said pharmaceutical composition will depend on the use to which the chosen compound of the formula (I) is to be put, and on other factors such as a preference in one of the areas of therapy for a particular mode of administration.

By way of illustration, the compositions may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agent, emulsifying agents, nonaqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization by exposure to ethylene oxide before suspending in the sterile vehicle. Advantageously, a surfactant or wetting agent is included in the composition to facilitate uniform distribution of the compound.

When appropriate for bronchodilation therapy, the compositions of this invention may be presented as an aerosol for inhalation administration, or as a microfine powder for insufflation.

As is common practice, the compositions will usually be accompaied by written or printed directions for use in the mdeical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment or propylaxis of disorders in human beings which comprises the administration to the sufferer of an effective amount of a compound of the formula (I).

The following Examples illustrate the preparation of compounds of the formula (I) and their pharmacological properties.

EXAMPLE 1

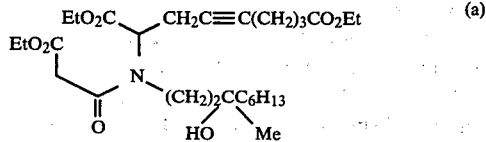

Ethyl 8-ethoxycarbonyl-2-[N-(3'-hydroxy-3'-methyl-n-nonyl)-N-ethoxycarbonyl-acetyl]amino-oct-4-yne-oate A solution of monoethyl malonate (3.99 g) in dry methylene chloride (100 ml) was added to a solution of ethyl-8-ethoxycarbonyl-2-[N-(3'-hydroxy-3'-methyl-n-nonyl)]amino-oct-4-yne-oate (12.41 g) in dry methylene chloride (100 ml). The mixture was stirred at 0° and a solution of dicyclohexylcarbodiimide (6.3 g) in dry methylene chloride (50 ml) was added dropwise. Stirring was continued overnight at room temperature.

The mixture was filtered through kieselguhr and the filtrate evaporated in vacuo. The residue was taken up in ether and the ethereal solution was washed with dilute hydrochloric acid, sodium bicarbonate solution and then with brine until the washings were neutral. The ethereal solution was dried ($Na_2SO_4$) and evaporated in vacuo to give an orange oil (14 g). The oil was chromatographed on silica gel (500 g) using chloroform as eluant to give ethyl 8-ethoxycarbonyl-2-[N-(3'-hydroxy-3'-methyl-n-nonyl)-N-ethoxycarbonyl-acetyl]amino-oct-4-yne-oate (6 g) as an orange oil.

EXAMPLE 1

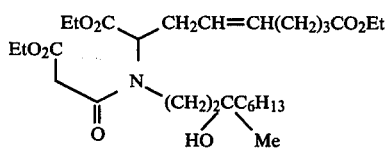

Ethyl 8-ethoxycarbonyl-2-[N-(3'-hydroxy-3'-methyl-n-nonyl)-N-ethoxycarbonyl-acetyl]amino-4-ene-oate 5% Palladium on calcium carbonate (0.3 g) and quinoline (0.3 ml) were added to a solution of ethyl 8-ethoxycarbonyl-2-[N-(3'-hydroxy-3'-methyl-n-nonyl)-N-ethoxycarbonyl-acetyl]amino-oct-4-yne-oate (6 g) in dry ethanol (100 ml) and the mixture was hydrogenated at room temperature and atmospheric pressure for 2 hours. The reaction mixture was filtered through kieselguhr and the filtrate evaporated in vacuo. The residual oil was partitioned between ether and dilute hydrochloric acid. The ether extract was washed with brine, dried ($Na_2SO_4$) and evaporated in vacuo to give ethyl 8-ethoxycarbonyl-2-[N-(3'-hydroxy-3'-methyl-n-nonyl)-N-ethoxycarbonyl-acetyl]amino-oct-4-ene-oate (5.5 g) as an orange oil.

I.R. spectrum—hydroxy absorption at 3450 $cm^{-1}$ ester carbonyl absorption at 1740 $cm^{-1}$ amide carbonyl absorption at 1660 $cm^{-1}$ Mass spectrum—$C_{28}H_{49}NO_8M^+$. Requires 527.3455 Found 527.3475

EXAMPLE 1

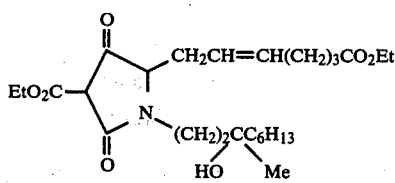

4-Ethoxycarbonyl-2-(6'-ethoxycarbonyl-n-hex-2'-enyl)-1-(3''-hydroxy-3''-methyl-n-nonyl)-pyrrolidin-3,5-dione Potassium tert-butoxide (1.2 g) was added in small portions over 30 minutes to a warm solution of ethyl 8-ethoxycarbonyl-2-[N-(3'-hydroxy-3'-methyl-n-nonyl)-N-ethoxycarbonyl-acetyl]amino-oct-4-ene-oate (5.5 g) in dry THF (100 ml) under nitrogen. The mixture was gently refluxed for 1 hour.

The solvent was evaporated in vacuo and the residue was taken up in water. The solution was extracted twice with ether and the aqueous layer was acidified to pH3 with dilute hydrochloric acid and extracted with ether. This ethereal solution was washed with brine and dried over magnesium sulphate to give a solution of 4-ethoxycarbonyl-2-(6'-ethoxycarbonyl-n-hex-2'-enyl)-1-(3''-hydroxy-3''-methyl-n-nonyl)-pyrrolidin-3,5-dione.

EXAMPLE 1

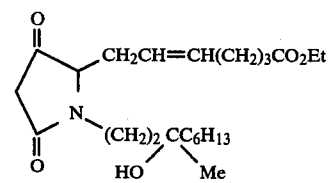

2-(6'-Ethoxycarbonyl-n-hex-2'-enyl)-1-(3''-hydroxy-3''-methyl-n-nonyl)-pyrrolidin-3,5-dione A solution of 4-ethoxycarbonyl-2-(6'-ethoxycarbonyl-n-hex-2'-enyl)-1-(3''-hydroxy-3''-methyl-n-nonyl)-pyrrolidin-3,5-dione in ether was stirred overnight in the presence of magnesium sulphate. The solution was filtered and the filtrate evaporated to give 2-(6'-ethoxycarbonyl-n-hex-2'-enyl)-1-(3''-hydroxy-3''-methyl-n-nonyl)-pyrrolidin-3,5-dione (2.5 g) as a yellow oil I.R. spectrum—broad OH absorption at 3450 $cm^{-1}$ amide carbonyl absorption at 1680 $cm^{-1}$ ester carbonyl absorption at 1730 $cm^{-1}$ carbonyl absorption at 1770 $cm^{-1}$

EXAMPLE 1

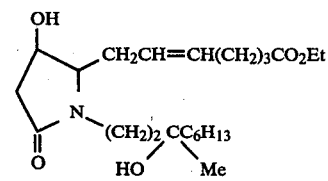

2-(6'-Ethoxycarbonyl-n-hex-2'-enyl)-3-hydroxy-1-(3''-hydroxy-3''-methyl-n-nonyl)pyrrolidin-5-one Lithium perhydro-9b-boraphenalylhydride (25 ml; 0.5 M solution in tetrahydrofuran) was added dropwise to a stirred solution of 2-(6'-ethoxycarbonyl-n-hex-2'-enyl)-1-(3''-hydroxy-3''-methyl-n-nonyl)-pyrrolidin-3,5-dione (2.5 g) in dry tetrahydrofuran (30 ml) under nitrogen at −78°. After 1 hour water was added and the mixture was allowed to warm to room temperature. Ether was added to the reaction mixture and the organic phase was washed with brine, dried ($Na_2SO_4$) and evaporated in vacuo to give a yellow gum. The gum was purified on silica gel (200 g) using chloroform, chloroform/2% methanol and chloroform/4% methanol as successive eluants to give 2-(6'-ethoxycarbonyl-n-hex-2'-enyl)-3-hydroxy-1-(3''-hydroxy-3''-methyl-n-nonyl)-pyrrolidin-5-one (0.5 g) as a yellow gum.

I.R. spectrum—broad OH absorption at 3400 $cm^{-1}$ ester carbonyl absorption at 1730 $cm^{-1}$ amide carbonyl absorption at 1660 $cm^{-1}$

EXAMPLE 1

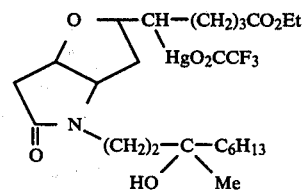

2-(1'-Mercury trifluoroacetate-4'-ethoxycarbonyl-n-butyl)-4-(3''-hydroxy-3''-methyl-n-nonyl)-5-oxo-5H-hexahydro-furo[3,2-b]pyrrole Mercuric (II) trifluoroacetate (481 mg) was added to a stirred solution of 2-(6'-ethoxycarbonyl-n-hex-2'-enyl)-3-hydroxy-1-(3''-hydroxy-3''-methyl-n-nonyl)-pyrrolidin-5-one (385 mg) in dry tetrahydrofuran (10 ml) containing a suspension of calcium carbonate (111 mg). The reaction mixture was stirred for 1 hour at room temperature and then filtered and evaporated in vacuo to give 2-(1'-mercury trifluoroacetate-4'-ethoxycarbonyl-n-butyl)-4-(3''-hydroxy-3''-methyl-n-nonyl)-5-oxo-5H-hexahydro-furo[3, 2-b]pyrrole (450 mg) as a pale yellow oil.

EXAMPLE 1

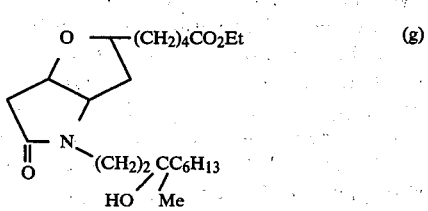

(g)

2-(4'-Ethoxycarbonyl-n-butyl)-4-[3''-hydroxy-3''-methyl-n-nonyl]-5-oxo-5H-hexahydro-furo[3,2-b]pyrrole (Compound 1)

Sodium borohydride (50 mg) was added in one portion to a stirred solution of 2-(1'-mercury trifluoroacetate-4'-ethoxycarbonyl-n-butyl)-4-(3''-hydroxy-3''-methyl-n-nonyl)-5-oxo-5H-hexahydro-furo[3,2-b]pyrrole (450 mg) in dry ethanol (10 ml) as −20°.

The solution was stirred for 1 hour and then partitioned between dilute hydrochloric acid and ether, the ethereal layer was washed with brine, dried (Na$_2$SO$_4$) and evaporated in vacuo to give a yellow oil. The oil was purified on silica gel (50 g) using chloroform as eluant to give 2-(4'-ethoxycarbonyl-n-butyl)-4-(3''-hydroxy-3''-methyl-n-nonyl)-5-oxo-5H-hexahydrofuro[3,2-b]pyrrole (180 mg) as a pale yellow oil.

I.R. spectrum—broad OH absorption at 3400 cm$^{-1}$ ester carbonyl absorption at 1730 cm$^{-1}$ amide carbonyl absorption at 1680 cm$^{-1}$ Mass spectrum—C$_{23}$H$_{41}$NO$_5$M$^+$. Requires 411.2982 Found 411.2979

EXAMPLE 2

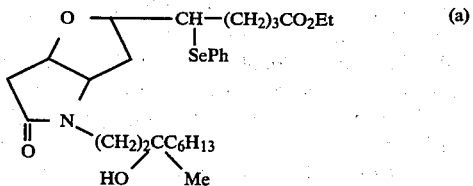

(a)

2-(1-Phenylseleno-4'-ethoxycarbonyl-n-butyl)-4-(3''-hydroxy-3''-methyl-n-nonyl)-5-oxo-5H-hexahydro-furo[3,2-b]pyrrole.

Phenyl selenyl chloride (558 mg) was added to a stirred solution of 2-(6'-ethoxycarbonyl-n-hex-2'-enyl)-3-hydroxy-1-(3''-hydroxy-3''-methyl-n-nonyl)-pyrrolidin-5-one (1 g) in dry tetrahydrofuran (20 ml) containing a suspension of calcium carbonate (243 mgs) at −20°. The solution was stirred for 10 minutes at −20° and then for 1 hour at 0°. The reaction mixture was then filtered to give a solution of 2-(1'phenylseleno-4'-ethoxycarbonyl-n-butyl)-4-(3''-hydroxy-3''-methyl-n-nonyl)-5-oxo-5H-hexahydro-furo[3,2-b]pyrrole.

EXAMPLE 2

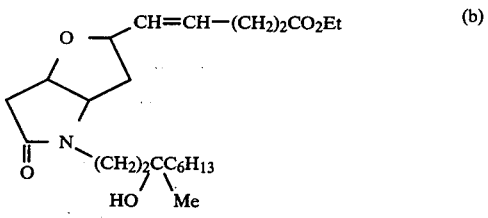

(b)

2-(4'-Ethoxycarbonyl-n-but-1'-enyl)-4-(3''-hydroxy-3''-methyl-n-nonyl-5-oxo-5H-hexahydro-furo [3,2-b] pyrrole (Compound 2)

Hydrogen peroxide (2.8 ml 30% w/v H$_2$O$_2$) was added dropwise to a stirred solution of 2-(1'-phenyl seleno-4'-ethoxycarbonyl-n-butyl)-4-(3''-hydroxy-3''-methyl-n-nonyl)-5-oxo-5H-hexahydro-furo[3, 2-b] pyrrole in tetrahydrofuran (20 ml) at −10°. The solution was stirred for a further 3 hours at room temperature. The reaction mixture was diluted with ether and the organic phase washed with brine (2×50 ml), dried (Na$_2$SO$_4$), and evaporated in vacuo to give a pale yellow oil. The oil was purified on silica gel (50 g) using chloroform as eluant to give 2-(4'-ethoxycarbonyl-n-but-1'-enyl)-4-(3''-hydroxy-3''-methyl-n-nonyl)-5-oxo-5H-hexahydro-furo [3, 2-b] pyrrole (60 mg) as a colourless oil.

I.R. Spectrum - broad OH absorption at 3400 cm$^{-1}$ ester carbonyl absorption at 1730 cm$^{-1}$ amide carbonyl absorption at 1680 cm$^{-1}$ Mass spectrum—C$_{23}$H$_{39}$NO$_5$ M$^+$· requires 409.2826 found 409.2803

EXAMPLE 3

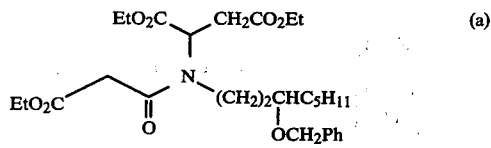

(a)

Diethyl 2-[N-(3'-benzyloxy-n-octyl)-N-ethoxycarbonyl-acetyl] aminosuccinate

A solution of monoethyl malonate (28.2 g, 0.213 mole) in dry methylene chloride (150 ml) was added to a solution of diethyl 2-[N-(3'-benzyloxy-n-octyl)-aminosuccinate (87 g, 0.213 mole) in dry methylene chloride (250 ml). The mixture was stirred at 0° and a solution of dicyclohexylcarbodiimide (43.8 g, 0.213 mole) in dry methylene chloride (250 ml) was added dropwise. Stirring was continued overnight at room temperature. The mixture was filtered and the filtrate was evaporated in vacuo. The residue was dissolved in ether and the ethereal solution was washed with dilute hydrochloric acid, then sodium bicarbonate solution, and finally with brine until the washings were natural. The ethereal solution was dried (MgSO$_4$) and evaporated in vacuo to give an organge oil. The crude product was dissolved in petroleum ether (b.p. 40°-60°) and the solution was filtered. Evaporation of the filtrate gave the triester as an orange oil (96 g, 86%) which was used without further purification.

A sample purified by chromatography on silica gel had the following physical characteristics.

I.R. spectrum—ester carbonyl absorption at 1730 cm$^{-1}$ amide carbonyl absorption at 1655 cm$^{-1}$ Mass spectrum—C$_{28}$H$_{43}$NO$_8$ M$^+$· Requires 521.2988 Found 521.3020

EXAMPLE 3

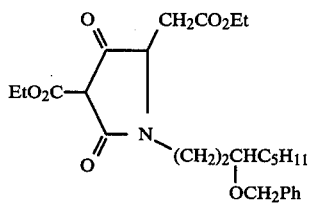 (b)

1-(3'-Benzyloxy-n-octyl)4-ethoxycarbonyl-2-(ethoxycarbonylmethyl)pyrrolidin-3,5-dione Potassium tert butoxide (20.6 g., 0.184 mole) was added in small portions over 45 min to a solution of diethyl 2-[N-(3'-benzyloxy-n-octyl)-N-ethoxycarbonylacetyl]aminosuccinate (96 g., 0.184 mole) in dry tetrahydrofuran (200 ml) at 30°–40°. The mixture was gently refluxed for 1½ hr. The solvent was evaporated in vacuo and the residue was taken up in water. The solution was extracted twice with ether and the aqueous layer was acidified (pH 3) with dilute hydrochloric acid. The resulting solution was extracted with ether, and the organic layer was washed with brine and dried briefly over magnesium sulphate to give a solution of 1-(3'-benzyloxy-n-octyl)-4-ethoxycarbonyl-2-(ethoxycarbonylmethyl)-pyrrolidin-3,5-dione.

EXAMPLE 3

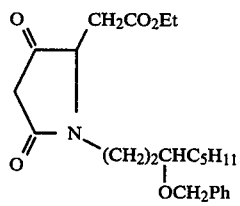 (c)

1-(3'-Benzyloxy-n-octyl)-2-(ethoxycarbonylmethyl)-pyrrolidin-3,5-dione

The solution of 1-(3'-benzyloxy-n-octyl)-4-ethoxycarbonyl-2-(ethoxycarbonylmethyl)-pyrrolidin-3,5-dione in ether (obtained as described above) was stirred overnight in the presence of magnesium sulphate. The mixture was filtered and the filtrate was evaporated in vacuo giving 1-(3'-benzyloxy-n-octyl)-2-(ethoxycarbonylmethyl)pyrrolidin-3,5-dione [71 g., 95% overall yield for steps b) and c)] as a yellow oil.

A sample purified by chromatography on silica gel had the following physical characteristics.

I.R. spectrum—amide carbonyl absorption at 1685 cm$^{-1}$ ester carbonyl absorption at 1730 cm$^{-1}$ carbonyl absorption at 1770 cm$^{-1}$ Mass spectrum—C$_{22}$H$_{33}$NO$_5$ M$^+$· Requires 403.2358 Found 403.2352

EXAMPLE 3

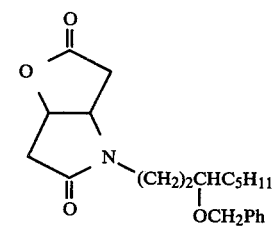 (d)

4-(3'-Benzyloxy-n-octyl)perhydrofuro[3.2-b]pyrrolidin-2,5-dione

A solution of potassium hydroxide (66 g., 1.17 mole) in ethanol (660 ml) was added to 1-(3'-benzyloxy-n-octyl)-2-(ethoxycarbonylmethyl) pyrrolidin-3,5-dione (66 g., 0.163 mole) at room temperature and the solution was allowed to stand overnight.

This reaction mixture was cooled to 0°–5° and sodium borohydride (9.3 g., 0.24 mole) was added in small portions with stirring. The mixture was stirred at 0°–5° for 1 hr., then acidified (pH 2) by dropwise addition of dilute hydrochloric acid. The solvent was removed in vacuo, the residue was dissolved in ether and the solution was dried (MgSO$_4$), filtered and evaporated giving an orange oil. The product was purified on silica gel (1 kg) using a mixture of 60°–80° petroleum ether, chloroform and methanol (50:49:1) as eluant. 4-(3'-Benzyloxy-n-octyl)perhydrofuro[3.2-b]pyrrolidin-2,5-dione (35 g., 60%) was obtained as pale yellow oil.

I.R. spectrum—amide carbonyl at 1690 cm$^{-1}$ lactone carbonyl at 1785 cm$^{-1}$ Mass spectrum—C$_{21}$H$_{30}$NO$_4$ MH$^+$ Requires 360.2175 Found 360.2168

EXAMPLE 3

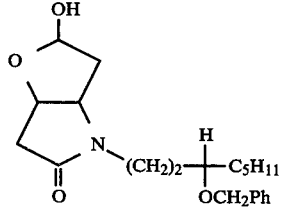 (e)

4-(3'-Benzyloxy-n-octyl)perhydrofuro[3,2-b]pyrrol-2-ol-5-one

To a solution of 4-(3'-benzyloxy-n-octyl)perhydrofuro[3,2-b]-pyrrol-2,5-dione (35.0 g., 0.097 mole) in dry tetrahydrofuran (350 ml) was added lithium tri- tert butoxyaluminohydride (74.4 g., 0.29 mole) in small portions over 30 min. at 3°–5°. The mixture was allowed to come slowly to room temperature (40 min), then stirred for a further 2 hr. The solution was acidified with dilute hydrochloric acid (ca. 2 N, 360 ml) below 15° and the resulting mixture was extracted with ether (3×250 ml). The combined organic extracts were washed with brine and dried (Na$_2$SO$_4$). Evaporation of the solvent gave a pale orange oil which was purified by chromatography on silica gel (800 g) using eluant consisting of 60°–80° petroleum ether (50 parts), chloroform (45 parts) and methanol (5 parts). The pure lactol was obtained as a pale yellow oil (22.3 g., 63.4%).

I.R. spectrum—amide carbonyl at 1665 cm$^{-1}$ broad OH absorption at 3360 cm$^{-1}$ Mass spectrum—$C_{21}H_{32}NO_4$ MH+ Requires 362.2331 Found 362.2326

EXAMPLE 3

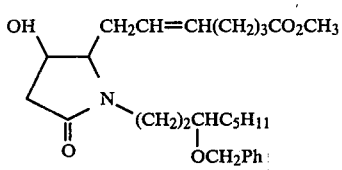

(f)

1-(3''-Benzyloxy-n-octyl-3-hydroxy-2-(6'-methoxycarbonyl-n-hex-2'-enyl)-pyrrolidin-5-one To a stirred solution of 4-(3'-benzyloxy-n-octyl)-perhydro-furo[3,2-b]pyrrol-2-ol-5-one (7.5 g., 0.02 mole) in dry tetrahydrofuran (77 ml) was added by syringe 77 ml of a solution of the ylid resulting from sodium methylsulphinylmethide in dimethyl sulphoxide (40 ml of a 4 M solution) and (4-carboxybutyl)triphenylphosphonium bromide (26.58 g., 0.06 mole) in dimethylsulphoxide (75 ml), as prepared by the method of Corey [Bindra J. S. and Bindra R., "Prostaglandin Synthesis" (New York 1977), p.210]. The resulting solution was stirred under nitrogen at room temperature for 3 hours. The reaction was quenched by adding water (10 ml), a further 290 ml of water was added, and the mixture extracted with ethyl acetate (3×250 ml). The aqueous layer was acidified to pH 2 with dilute hydrochloric acid and extracted with ethyl acetate (2×250 ml). The organic layers were combined, washed with brine and dried (MgSO4). The ethyl acetate was removed under reduced pressure and the residue triturated with diethyl ether (3×200 ml). The ether solutions were filtered, the solvent evaporated and the combined residue dissolved in methanol and treated with ethereal diazomethane (1.5 equivalents). The solvents were removed under reduced pressure to give a brown oil (7.6 g). This product was purified by column chromatography on silica gel (500 g), using a mixture of 60°-80° petroleum ether, chloroform and methanol (ratio 20:19:1) as eluant. The ester was obtained as a pale yellow oil (5.42 g, 57%).

I.R. spectrum—broad OH absorption at 3350 cm$^{-1}$ ester carbonyl absorption at 1735 cm$^{-1}$ amide carbonyl absorption at 1670 cm$^{-1}$ Mass spectrum—$C_{27}H_{41}NO_5$ M+ Requires 459.2985 Found 459.3009

EXAMPLE 3

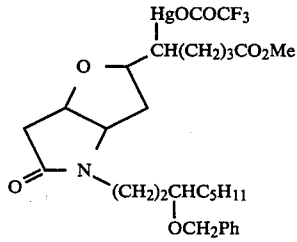

(g)

4-(3''-Benzyloxy-n-octyl)-2-(1'-mercury trifluoroacetate-4'-methoxycarbonyl-n-butyl)-5-oxo-5H-hexahydrofuro[3,2-b]pyrrole.

Mercuric (II) trifluoroacetate (3.34 g., 0.0078 mole) was added to a stirred solution of 1-(3''-benzyloxy-n-octyl)-3-hydroxy-2-(6'-methoxycarbonyl-n-hex-2'-enyl)-pyrrolidin-5-one (3.0 g., 0.0065 mole) in dry tetrahydrofuran (20 ml) containing a suspension of calcium carbonate (0.8 g., 0.008 mole). The reaction mixture was stirred at room temperature for 1 hour, filtered and evaporated in vacuo to give the mercuri compound as a yellow oil (6.0 g., 99%) which was used without further purification.

EXAMPLE 3

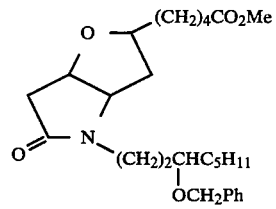

(h)

4-(3''-Benzyloxy-n-octyl)-2-(4'-methoxycarbonyl-n-butyl)-5-oxo-5H-hexahydrofuro[3,2-b]pyrrole Sodium borohydride (0.88 g., 0.023 mole) was added in two portions to a stirred solution of 4-(3''-benzyloxy-n-octyl)-2-(1'-mercury trifluoroacetate-4'-methoxycarbonyl-n-butyl)-5-oxo-5H-hexahydrofuro[3,2-b]pyrrole (6.0 g., 0.0078 mole) in dry ethanol (30 ml) at −20°.

The solution was stirred for 1 hour at −20° and then partitioned between dilute hydrochloric acid and ether. The ethanol layer was washed with brine, dried (MgSO4) and evaporated in vacuo to give a pale yellow oil (2.8 g). The oil was purified on silica gel (120 g) using chloroform as eluant, yielding 4-(3''-benzyloxy-n-octyl)-2-(4'-methoxycarbonyl-n-butyl)-5-oxo-5H-hexahydrofuro[3,2-b]pyrrole as a pale yellow oil (1.52 g., 50%).

I.R. spectrum—ester carbonyl absorption at 1740 cm$^{-1}$ amide carbonyl absorption at 1690 cm$^{-1}$ Mass spectrum—$C_{27}H_{42}NO_5$ MH+ Requires 460.3063 Found 460.3049

EXAMPLE 3

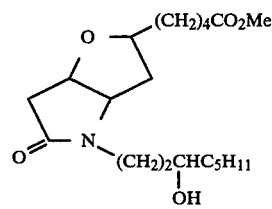

(i)

4-(3''-Hydroxy-n-octyl)-2-(4'-methoxycarbonyl-n-butyl)-5-oxo-5H-hexahydrofuro[3,2-b]pyrrole 4-(3''-Benzyloxy-n-octyl)-2-(4'-methoxycarbonyl-n-butyl)-5-oxo-5H-hexahydrofuro[3,2-b]pyrrole (1.0 g, 0.002 mole) was dissolved in dimethoxyethane (25 ml) and 10% palladium on charcoal catalyst (ca 0.3 g) was added. The mixture was stirred under 1 atmosphere of hydrogen at room temperature for ca 2 hours until the theoretical volume of hydrogen (50 ml) had been taken up. The reaction mixture was filtered through celite and the catalyst was washed well with dichloromethane. The filtrate was evaporated in vacuo to give 4-(3''-hydroxy-n-octyl)-2-(4'-methoxycarbonyl-n-butyl)5-oxo-5H-hexahydrofuro[3,2-b]pyrrole (0.8 g, 99%) as a pale yellow oil.

I.R. Spectrum—broad OH absorption at 3400 cm$^{-1}$ ester carbonyl absorption at 1735 cm$^{-1}$ amide carbonyl absorption at 1670 cm$^{-1}$ Mass Spectrum—$C_{20}H_{35}NO_5$ M+· Requires: 369.2515 Found: 369.2520

EXAMPLE 4

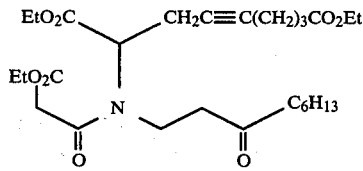 (a)

In a similar manner to example 1a ethyl 8-ethoxycarbonyl-2-[N-(3-oxo-n-nonyl)-N-ethoxycarbonylacetyl]amino-oct-4-ynoate was prepared from ethyl 8-ethoxycarbonyl-2-[N-(3-oxo-n-nonyl)]amino-oct-4-ynoate and monoethylmalonate.

I.R. (film; cm$^{-1}$): 1740 [CO$_2$Et]; 1710 (shoulder) [C=O]; 1660 [CON<].

NMR (CDCl$_3$; $\tau$): 7.65, m, 6H, [CH$_2$CO$_2$Et; CH$_2$C≡CCH$_2$]; 7.2, m, 4H, [CH$_2$COCH$_2$]; 6.55, s, 2H, [EtO$_2$CCH$_2$CON<]; 6.5, centre of brm, [NCH$_2$]; 5.9, m, 7H, [3×CO$_2$CH$_2$CH$_2$;NCH]

EXAMPLE 4

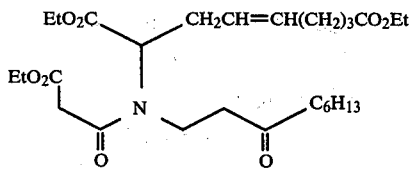 (b)

In a similar manner to example 1b, ethyl 8-ethoxycarbonyl-2-[N-(3-oxo-n-nonyl)-N-ethoxycarbonylacetyl]amino-oct-4-enoate was prepared from ethyl 8-ethoxycarbonyl-2-[N-(3-oxo-n-nonyl)-N-ethoxycarbonylacetyl]amino-oct-4-ynoate.

The product was purified, via column chromatography, on silica gel (15:1) using 20% ethyl acetate/pentane as eluant.

NMR (CCl$_4$: $\tau$): 8.0, centre of brm, 6H, [CH$_2$CH=CHCH$_2$; CH$_2$CO$_2$Et]; 7.4, m, 4H, [CH$_2$COCH$_2$]; 6.75, brm, 4H, [NCH$_2$; EtO$_2$CCH$_2$CON<]; 5.9, m, 7H, [3×CO$_2$CH$_2$CH$_3$; NCH]; 4.6, bm, 2H, [CH=CH].

EXAMPLE 4

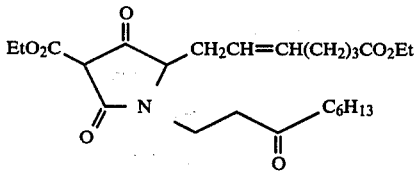 (c)

In a similar manner to example 1c, 4-ethoxycarbonyl-2-(6'-ethoxycarbonyl-n-hex-2'-enyl)-1-(3''-oxo-n-nonyl) pyrrolidin-3,5-dione was prepared from ethyl 8-ethoxycarbonyl-2-[N-(3-oxo-n-nonyl)-N-ethoxycarbonylacetyl]amino-oct-4-enoate.

EXAMPLE 4

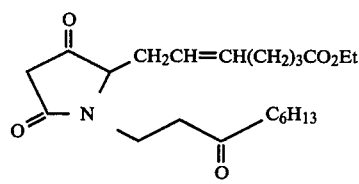 (d)

In a similar manner to example 1d, 2-(6'-ethoxycarbonyl-n-hex-2'-enyl)-1-(3''-oxo-n-nonyl) pyrrolidin-3,5-dione was prepared from 4-ethoxycarbonyl-2-(6'-ethoxycarbonyl-n-hex-2'-enyl)-1-(3''-oxo-n-nonyl)pyrrolidin-3,5-dione.

EXAMPLE 4

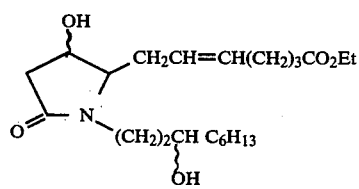 (e)

Sodium borohydride (1.26 g; 2.2 mol. equiv.) was added in portions to a stirred solution of 2-(6'-ethoxycarbonyl-n-hex-2'-enyl)-1-(3''-oxo-n-nonyl) pyrrolidin-3,5-dione (5.7 g) in ethanol (80 ml). The mixture was stirred at room temperature for 3 hours then the ethanol was evaporated in vacuo at ≦30° C. The residue was partitioned between very dilute hydrochloric acid and ether. The ether solution was washed with 5% sodium bicarbonate solution and with brine then was dried and evaporated in vacuo. The resulting yellow oil was purified via column chromatographt on silica gel (20:1) using ethyl acetate as euluant to give 1-(3'-hydroxy-n-nonyl)-2-(6''-ethoxycarbonyl-n-hex-2-enyl)-3-hydroxy-pyrrolidin-5-one (2.45 g) as a colourless gum.

I.R. (film; cm$^{-1}$): 3370 (OH); 1730 (CO$_2$Et); 1670 (CON>).

NMR (CDCl$_3$; $\tau$): 7.7, centre of brm, 8H, [CH$_2$CH=CHCH$_2$; NCOCH$_2$; CH$_2$CO$_2$Et]; 6.5, centre of brm, 6H, [CHOH×2; NCH$_2$]; 5.9, q, 2H, [CO$_2$CH$_2$CH$_3$]; 4.5, m, 2H, [CH=CH].

EXAMPLE 4

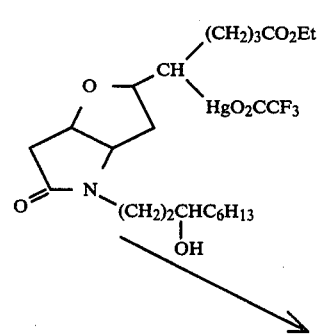 (f)

-continued

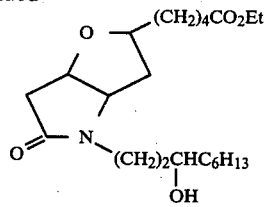

Mercuric (II) trifluoroacetate (2.83 g; 1.2 mol. equiv.) was added in portions during 15 mins. to a solution of 1-(3'-hydroxy-n-nonyl)-2-(6''-ethoxycarbonyl-n-hex-2-enyl)-3-hydroxy-pyrrolidin-5-one (2.2 g) in dry tetrahydrofuran (25 ml) containing a suspension of calcium carbonate (665 mg; 1.2 mol. equiv.). The mixture was stirred at room temperature for 3 hours then was evaporated in vacuo at $\leq 30°$ C. The residue which contained 2-(1'-mercury trifluoroacetate-4'-ethoxycarbonyl-n-butyl)-4-(3''-hydroxy-n-nonyl)-5-oxo-5H-hexahydrofuro[3,2-b]pyrrole was stirred in dry ethanol (50 ml) at $-78°$ C. Sodium borohydride (253 mg; 1.2 mol. equiv.) was added in portions over 15 mins. and then the cooling bath was removed. The resulting mixture was stirred for 1 hour then the ethanol was evaporated in vacuo at 30° C. The residue was partitioned between very dilute hydrochloric acid and ether. The ether solution was washed with 5% sodium bicarbonate solution and with brine then was dried and evaporated in vacuo to give a pale yellow gum (1.96 g). This was shown by TLC (silica plates in ethyl acetate) to be a mixture of two components. These were separated via column chromatography on silica gel (30:1) using ethyl acetate as eluant and were shown to be diastereoisomers of 2-(4'-ethoxycarbonyl-n-butyl)-4-(3''-hydroxy-n-nonyl)-5-oxo-5H-hexahydrofuro[3,2b]pyrrole.

The higher $R_f$ component ($R_f \approx 0.38$) (560 mg) was obtained as a pale yellow oil.

I.R. (film; cm$^{-1}$): 3400 (OH); 1730 (CO$_2$Et); 1660 (CON>).

NMR (CDCl$_3$; $\tau$): 7.75, m, 2H, [CH$_2$CO$_2$=CH$_5$]; 7.45, m, 2H, [CH$_2$CON]; 7.0, b, 1H, [OH];

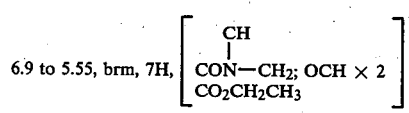

5.3, m, 1H, [OCHCHNCO]

Mass Spectrum: C$_{22}$H$_{29}$NO$_5$ (M+) requires: 397.2828 found: 397.2816

The lower $R_f$ component ($R_f \approx 0.32$) (450 mg) was obtained as a pale yellow gum.

NMR (CDCl$_3$; $\tau$): 7.75, m, 2H, [CH$_2$CO$_2$Et]; 7.45, m, 2H, [CH$_2$CON];

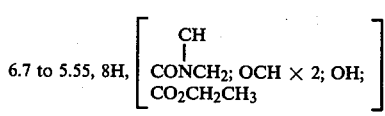

5.35, m, 1H, [OCHCHNC=O].

Mass Spectrum: C$_{22}$H$_{39}$NO$_5$ (M+) requires: 397.2828 found: 397.2830.

EXAMPLE 5

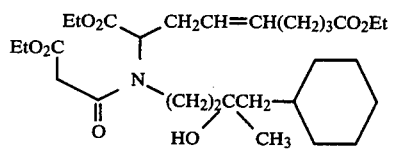

(a)

In a similar manner to example 1b, ethyl 8-ethoxycarbonyl-2-[N-(3'-hydroxy-3'-methyl-4'-cyclohexyl-n-butyl)-N-ethoxycarbonylacetyl]amino-oct-4-enoate was prepared from ethyl 8-ethoxycarbonyl-2-[N-(3'-hydroxy-3'-methyl-4'-cyclohexyl-n-butyl)-N-ethoxycarbonylacetyl]amino-oct-4-ynoate.

I.R. (film, cm$^{-1}$): 3450 (OH); 1740 (CO$_2$Et); 1670 (CON>).

NMR (CDCl$_3$; $\tau$): 6.5, s, 2H, [EtO$_2$CCH$_2$CON>]; 6.1 to 5.5, m, 7H, [CO$_2$CH$_2$CH$_3$×3; NCH]; 4.55, bm, 2H, [CH=CH].

This product was converted into 1-(3'-hydroxy-3'-methyl-4'-cyclohexyl-n-butyl)-2-(6''-ethoxycarbonyl-n-hex-2''-enyl)pyrrolidin-3,5-dione in a similar manner to that described in examples 1c and 1d.

EXAMPLE 5

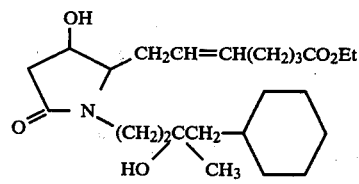

(b)

In a similar manner to example 4e, (but using 1.1 mol. equiv. of sodium borohydride), 1-(3'-hydroxy-3'-methyl-4'-cyclohexyl-n-butyl)-2-(6''-ethoxycarbonyl-n-hex-2''-enyl)-3-hydroxy pyrrolidin-5-one was prepared from 1-(3'-hydroxy-3'-methyl-4'-cyclohexyl-n-butyl)-2-(6''-ethoxycarbonyl-n-hex-2''-enyl)pyrrolidin-3,5-dione.

I.R. (film; cm$^{-1}$): 3400 (OH); 1740 (CO$_2$Et); 1670 (CON>).

NMR (CDCl$_3$; $\tau$): 7.7, centre of brm, 8H, [CH$_2$CH=CHCH$_2$]; 7.25, bs, 1H, [OH]; 6.9 to 6.15, brm, 4H, [CHOH; NCH$_2$]; 5.95, q, 2H, [CO$_2$CH$_2$CH$_3$]; 4.55, m, 2H, [CH=CH].

Mass Spectrum: C$_{23}$H$_{38}$NO$_5$ (M+—CH$_3$) requires: 408.2750 found: 408.2760.

EXAMPLE 5

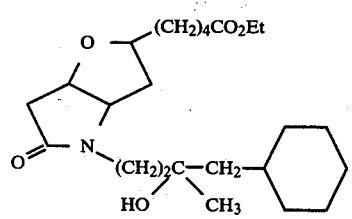

(c)

In a manner similar to example 4f, 2-(4'-ethoxycarbonyl-n-butyl)-4-(3''-hydroxy-3''-hydroxy-3''-methyl-4''-cyclohexyl-n-butyl)5-oxo-5H-hexahydro-furo [3-2b]pyrrole was prepared from 1-(3'-hydroxy-3'-methyl-4'-cyclohexyl-n-butyl)-2-(6''-ethoxycarbonyl-n-hex-2''-enyl)-3-hydroxy pyrolidin-5-one.

I.R. (film, cm$^{-1}$): 3400 (OH); 1735 (CO$_2$Et); 1665 (CON>).

NMR (CDCl$_3$; τ); 7.7, bs, 1H, [OH]; 7.65, m, 2H, [CH CO Et]; 7.45, m, 2H, [CH CON>];

7.2 to 5.6, m, 6H, [CONCH; OCH; CO CH CH];

5.4, m, 1H, [—OCHCHN<].

Mass Spectrum: C$_{23}$H$_{38}$NO$_5$ (M+-CH$_3$) requires: 408.2749 found: 408.2778.

Analysis: C$_{24}$H$_{41}$NO$_5$ requires: C, 68.05; H, 9.76; N, 3.31%; found: C, 68.01; H, 9.87; N, 3.15%.

EXAMPLE 6

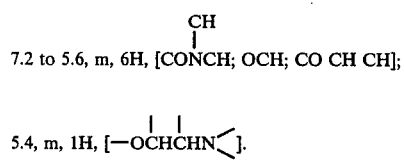
(a)

In a similar manner to example 1b, ethyl 9-ethoxycarbonyl-2-[N-(3'-hydroxy-3'-cyclohexyl-n-butyl)-N-ethoxycarbonylacetyl]amino-non-4-enoate was prepared from ethyl 9-ethoxycarbonyl-2-[N-(3'-hydroxy-3'-cyclohexyl-n-butyl)-N-ethoxycarbonylacetyl]amino-non-4-ynoate.

I.R. (film; cm$^{-1}$): 3450 (OH); 1740 (CO$_2$Et); 1660 (CON>).

NMR (CDCl$_3$; τ): 6.5, s, 2H, [EtO$_2$CCH$_2$CON>]; 6.1 to 5.5, m, 7H, [CO$_2$CH$_2$CH$_3$×3; NCH]; 4.6, bm, 2H, [CH=CH].

This product was converted into 1-(3'-hydroxy-3'-cyclohexyl-n-butyl)-2-(7''-ethoxycarbonyl-n-oct-2''-enyl)pyrrolidin-3,5-dione in a similar manner to that described in examples 1c and 1d.

EXAMPLE 6

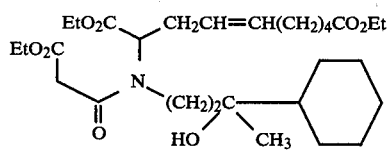
(b)

In a similar manner to example 5b, 1-(3'-hydroxy-3'-cyclohexyl-n-butyl)-2-(7''-ethoxycarbonyl-n-oct-2''-enyl)-3-hydroxy pyrrolidin-5-one was prepared from 1-(3'-hydroxy-3'-cyclohexyl-n-butyl)-2-(7''-ethoxycarbonyl-n-oct-2''-enyl)pyrrolidin-3,5-dione.

I.R. (film; cm$^{-1}$): 3410 (OH); 1740 (CO$_2$Et); 1670 (CON>).

NMR (CDCl$_3$; τ): 7.7, centre of brm, 8H [CH$_2$CH=CHCH$_2$; NCOCH$_2$; CH$_2$CO$_2$Et]; 6.5, brm, 4H, [CHOH, NCH$_2$]; 5.9, q, 2H, [CO$_2$CH$_2$CH$_3$]; 4.55, m, 2H, [CH=CH].

Mass Spectrum: C$_{23}$H$_{38}$NO$_5$ (M+-CH) requires: 408.2750 found: 408.2755.

EXAMPLE 6

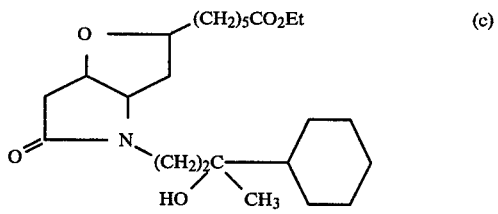
(c)

In a similar manner to example 4f, 2-(5'-ethoxycarbonyl-n-pentyl)-4-(3''-hydroxy-3''-cyclohexyl-n-butyl)-5-oxo-5H-hexahydro-furo[3,2b]pyrrole was prepared from 1-(3'-hydroxy-3'-cyclohexyl-n-butyl)-2-(7''-ethoxycarbonyl-n-oct-2''-enyl)-3-hydroxy pyrrolidin-5-one.

I.R. (film, cm$^{-1}$): 3400 (OH); 1735 (CO$_2$Et); 1665 (CON>).

NMR (CDCl$_3$; τ): 7.85, s, 1H, [OH]; 7.85, m, 2H, [CH$_2$CO$_2$Et]; 7.5, m, 2H, [CH$_2$CON>];

7.25 to 5.6, brm, 6H, [C(=O)—NCH$_2$; OCH; CO$_2$CH$_2$CH$_3$];

5.35, bm, 1H, [—OCHCHN<].

Mass Spectrum: C$_{24}$H$_{41}$NO$_5$ (M+) requires: 423.2984 found: 423.2980.

EXAMPLE 7

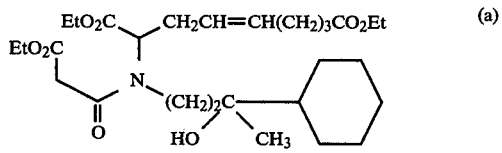
(a)

In a similar manner to example 1b, ethyl 8-ethoxycarbonyl-2-[N-(3'-hydroxy-3'-cyclohexyl-n-butyl)-N-ethoxycarbonyl acetyl]amino-oct-4-enoate was prepared from ethyl 8-ethoxycarbonyl-2-[N-(3'-hydroxy-3'-cyclohexyl-n-butyl)-N-ethoxycarbonylacetyl]amino-oct-4-ynoate.

I.R. (film; cm$^{-1}$): 3450 (OH); 1740 (CO$_2$Et); 1655 (CON>).

NMR (CDCl$_3$; τ): 6.6, m, 2H, [NCH$_2$];

6.5, bs, 2H, [EtO$_2$CCH$_2$CN<];

5.85, m, 7H, [CO$_2$CH$_2$CH$_3$ × 3; NCH];
4.6, m, 2H, [CH=CH].

This product was converted to 1(3'-hydroxy-3'-cyclohexyl-n-butyl)-2-(6''-ethoxycarbonyl-n-hex-2''-enyl) pyrrolidin-3,5-dione in a similar manner to that described in examples 1c and 1d.

EXAMPLE 7

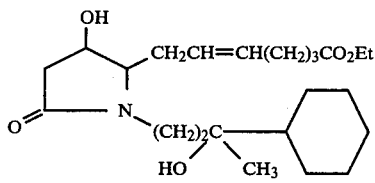 (b)

In a similar manner to example 5b, 1-(3'-hydroxy-3'-cyclohexyl-n-butyl)-2-(6''-ethoxycarbonyl-n-hex-2''-enyl)-3-hydroxy pyrrolidin-5-one was prepared from 1-(3'-hydroxy-3'-cyclohexyl-n-butyl)-2-(6''-ethoxycarbonyl-n-hex-2''-enyl)pyrrolidin 3,5-dione.

I.R. (film; cm$^{-1}$): 3400 (OH); 1740 (CO$_2$Et);

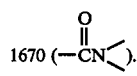

NMR (CCl$_4$; τ):

7.7, brm, 8H, [CH$_2$CH=CHCH$_2$; NCCH$_2$;
$\overset{O}{\overset{\|}{\phantom{C}}}$
CH$_2$CO$_2$Et];
6.5, brm, 4H, [CHOH; NCH$_2$];
5.95, q, 2H, [CO$_2$CH$_2$CH$_3$];
4.55, m, 2H, [CH=CH].

Mass Spectrum: C$_{23}$H$_{39}$NO$_5$ (M+) requires: 409.2827 found: 409.2801.

EXAMPLE 7

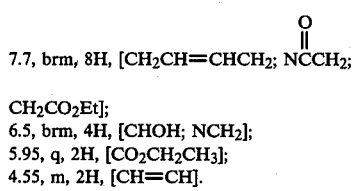 (c)

In a manner similar to example 4f, 2-(5'-ethoxycarbonyl-n-butyl)-4-(3''-hydroxy-3''-cyclohexyl-n-butyl)-5-oxo-5H-hexahydro-furo[3,2b]pyrrole was prepared from 1-(3'-hydroxy-3'-cyclohexyl-n-butyl)-2-(6''-ethoxycarbonyl-n-hex-2''-enyl)-3-hydroxypyrrolidin-5-one.

I.R. (film; cm$^{-1}$): 3420 (OH); 1735 (CO$_2$Et); 1670 (broad) (CON>).

NMR (CDCl$_3$; τ); 7.75, m, 2H, [CH$_2$CO$_2$Et];

7.45, bs, 3H, [OH; CH$_2$C(=O)N<];

7.3 to 5.6, brm, 6H, [C(=O)—NCH$_2$; OCH; CO$_2$CH$_2$CH$_3$];

5.4, bm, 1H, [—OCHCHN<].

Mass Spectrum: C$_{23}$H$_{39}$NO$_5$ (M+) requires: 409.2828 found: 409.2862

EXAMPLE 8

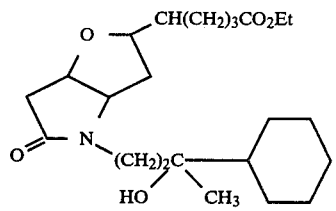

Potassium iodide (1.01 g; 1 mol. equiv.), sodium carbonate (0.713 g; 1.1 mol. equiv.) and iodine (3.1 g; 2 mol. equiv.) were added to a suspension of 1-(3'-hydroxy-3'-cyclohexyl-n-butyl)-2-(6''-ethoxycarbonyl-n-hex-2''-enyl)-3-hydroxy pyrrolidin-5-one in a mixture of ethanol (1 ml) and water (20 ml). The reaction mixture was stirred at 5° C. for 2 hours and the resultant brown solution was extracted with ether. The ether solution was washed with 5% sodium bicarbonate solution and with brine then was dried (Na$_2$SO$_4$; K$_2$CO$_3$) and evaporated in vacuo to give a dark brown oil (2 g). This was re-dissolved in dry benzene (40 ml) and 1,5-diazabicyclo[4.3.0]-non-5-ene[DBN] (2.3 g; 5 mol. equiv.) was added dropwise to the stirred solution. The mixture was stirred at room temperature for 25 hours then was diluted with ether. The organic phase was washed with ice-cold water, dried (K$_2$CO$_3$) and evaporated in vacuo to yield an orange coloured oil (325 mg). Attempted crystallisation via ether containing 3 drops of triethylamine gave a white crystalline solid (23 mg) and a dark yellow oil (293 mg) which partially solidified on cooling in the refrigerator. The solid was shown to be 2-(4'-ethoxycarbonyl-n-but-1'-idenyl)-4-(3''-hydroxy-3''-cyclohexyl-n-butyl)-5-oxo-5H-hexahydrofuro[3-2b]-yrrole.

I.R. (nujol; cm$^{-1}$): 3430 (OH); 1735 (CO$_2$Et); 1670 (CON>).

NMR (CCl$_4$; τ):

7.65 to 6.3, brm, 6H, [OH; CH$_2$C(=O)N<;

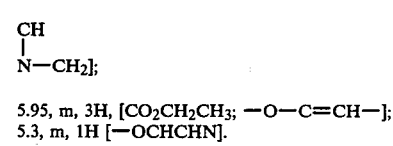

5.95, m, 3H, [CO$_2$CH$_2$CH$_3$; —O—C=CH—];
5.3, m, 1H [—OCHCHN].

Mass Spectrum: C$_{23}$H$_{37}$NO$_5$ (M+) requires: 407.2672 found: 407.2659.

The gum was shown via thin layer chromatography and mass spectral analysis to consist principally of the same compound (or its diastereoisomer).

Mass Spectrum: C$_{23}$H$_{37}$NO$_5$ (M+) requires: 407.2672 found: 407.2666.

PHARMACOLOGICAL DATA

1. Platelet Aggregation In Vitro Protocol

Human blood (20 ml) is drawn into a plastic syringe and immediately anti-coagulated by mixing with 0.1 volumes of 3.8% (w/v) trisodium citrate dihydrate. Platelet-rich plasma (P.R.P.) is prepared by centrifuging the anticoagulated blood of 180 g, for 12 minutes, at room temperature. Collagen "Collagen-reagent Horm" (Hormon-Chemie Munchem, Postfach 101, Germany)

is dilated as necessary with 0.9% (w/v) saline and kept on ice. Adenosine 5'-diphosphate (A.D.P.) (Grade 1: sodium salt from equine muscle, Sigma.) is diluted, as necessary with 0.9% saline, from a 10 mM stock solution, pH 6.8 kept at $-20°$ C. The compounds are dissolved freshly to 40 mM in dimethylformamide. P.R.P. is mixed with 0.1 volumes saline and 0.005 volumes compound on dimethylformamide (contröl) and incubated at 37° C. for 3 minutes before the addition of collagen.

Platelet aggregation in response to collagen and A.D.P. is measured photometrically (Born G.V.R., 1962, Nature, 194 927) in a Bryston aggregometer coupled to a Vitatron linear pen recorder. The concentration of collagen producing a just-maximal change in light transmittance and the concentration of A.D.P. to produce only a first-phase aggregation response are established in each control P.R.P. The concentration of compounds to inhibit these control response by 50% in each case are determined.

The results obtained are shown in Table 1 below.

TABLE 1

| Compound of Example No. | R | n | $R^1$ | $R^2$ | IC50 (μM) vs. collagen | IC50 (μM) vs. ADP |
|---|---|---|---|---|---|---|
| 1 | $C_2H_5$ | 4 | $C_6H_{13}$ | $CH_3$ | 8.8 | 35 |
| 3 | $CH_3$ | 4 | $C_5H_{11}$ | H | 1.7 | 4.9 |
| 4 (Higher Rf epimer) | $C_2H_5$ | 4 | $C_6H_{13}$ | H | 2.9 | 7.4 |
| 4 (Lower Rf epimer) | $C_2H_5$ | 4 | $C_6H_{13}$ | H | 28 | 120 |
| 5 | $C_2H_5$ | 4 | $-CH_2-\phi$ | $CH_3$ | 17 | 100 |
| 6 | $C_2H_5$ | 5 | $-\phi$ | $CH_3$ | 1.2 | 2.5 |

TABLE 1-continued

| Compound of Example No. | R | n | $R^1$ | $R^2$ | IC50 (μM) vs. collagen | IC50 (μM) vs. ADP |
|---|---|---|---|---|---|---|
| 7 | $C_2H_5$ | 4 | 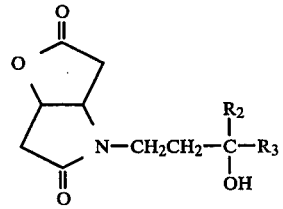 | $CH_3$ | 0.26 | 0.54 |

Bronchodilation Activity

1. The compounds were examined for their ability to inhibit 5-hydroxytryptamine induced bronchoconstriction in the anaesthetised, artificially respired guinea pig (Konzett-Rossler preparation). The compounds were administered intravenously. Compound 1 had an ED 50 of 131 μg/kg i.v. (mean of 3 experiments, ED 50 range 115-150 μg/kg).

2. The compounds were tested for their ability to inhibit histamine induced changes in pulmonary resistance and lung compliance in the anaesthetised spontaneously respiring guinea pig. The compounds were administered intravenously. The compound 1 had an ED 50 of 33 μg/kg i.v. against resistance changes and 46 μg/kg i.v. against compliance changes.

3. The compounds were also examined for their ability to protect conscious guinea pigs against bronchoconstriction induced by an histamine aerosol (Herxheimer test). In these experiments the compounds were administered by aerosol administration.

An aerosol of Compound 1 generated from a 100 μg/ml solution produced a highly significant protection against histamine challenge.

Toxicity

No toxic effects were observed at the given doses in either set of tests.

What we claim is:

1. A compound selected from the group consisting of a perhydrofuro[3,2-b]pyrrole of the formula:

and the benzyl ethers thereof,
wherein
$R_2$ is hydrogen or alkyl of 1 to 4 carbon atoms and
$R_3$ is alkyl of 4 to 9 carbon atoms, cycloalkyl of 5 to 7 carbon atoms or alkyl of 1 to 6 carbon atoms substituted with cycloalkyl of 5 to 7 carbon atoms.

* * * * *